United States Patent
McCluskey et al.

(10) Patent No.: US 11,639,393 B2
(45) Date of Patent: May 2, 2023

(54) ANTI-CCR8 ANTIBODIES

(71) Applicant: AbbVie Inc., North Chicago, IL (US)

(72) Inventors: Andrew J. McCluskey, Holden, MA (US); Amanda M. Schmidt Paustian, Vernon Hills, IL (US); Jane Seagal, San Diego, CA (US); Julie L. Wilsbacher, Round Lake Beach, IL (US)

(73) Assignee: AbbVie Inc.

( * ) Notice: Subject to any disclaimer, the term of this patent is extended or adjusted under 35 U.S.C. 154(b) by 0 days.

(21) Appl. No.: 17/815,505

(22) Filed: Jul. 27, 2022

(65) Prior Publication Data

US 2023/0048553 A1 Feb. 16, 2023

Related U.S. Application Data

(60) Provisional application No. 63/226,118, filed on Jul. 27, 2021.

(51) Int. Cl.
| | |
|---|---|
| *C07K 16/28* | (2006.01) |
| *A61P 35/00* | (2006.01) |
| *C12N 15/85* | (2006.01) |
| *A61K 39/00* | (2006.01) |

(52) U.S. Cl.
CPC .......... *C07K 16/2866* (2013.01); *A61P 35/00* (2018.01); *C12N 15/85* (2013.01); *A61K 2039/505* (2013.01); *A61K 2039/545* (2013.01); *A61K 2039/55* (2013.01); *C07K 2317/41* (2013.01); *C07K 2317/52* (2013.01); *C07K 2317/565* (2013.01); *C07K 2317/732* (2013.01)

(58) Field of Classification Search
CPC ............ C07K 16/2866; C07K 2317/41; C07K 2317/52; A61P 35/00; C12N 15/85
See application file for complete search history.

(56) References Cited

U.S. PATENT DOCUMENTS

| | | |
|---|---|---|
| 10,087,259 B1 | 10/2018 | Rudensky et al. |
| 10,550,191 B2 | 2/2020 | Yoshida et al. |
| 2021/0238292 A1 | 8/2021 | Holland et al. |
| 2021/0277129 A1* | 9/2021 | McGrath ............ C07K 16/2866 |
| 2022/0064312 A1 | 3/2022 | Yoshikawa et al. |

FOREIGN PATENT DOCUMENTS

| | | |
|---|---|---|
| WO | 2017198631 A1 | 11/2017 |
| WO | 2018112032 A1 | 6/2018 |
| WO | 2021163064 A2 | 8/2021 |
| WO | 2021178749 A2 | 9/2021 |
| WO | 2021194942 A1 | 9/2021 |
| WO | 2021260206 A2 | 12/2021 |
| WO | 2022003156 A1 | 1/2022 |
| WO | 2022042690 A1 | 3/2022 |
| WO | 2022078277 A1 | 4/2022 |
| WO | 2022081718 A1 | 4/2022 |
| WO | 2022136647 A1 | 6/2022 |
| WO | 2022136649 A1 | 6/2022 |

OTHER PUBLICATIONS

Campbell, J. R. et al., "Fc-Optimized Anti-CCR8 Antibody Depletes egulatory T Cells in Human Tumor Models'" Cancer Research (2021); vol. 81, pp. 2983-2994.
Plitas, G. et al., "Regulatory T Cells Exhibit Distinct Features in Human Breast Cancer", Immunity (2016); vol. 45, pp. 1122-1134.
Tanaka, A. et al., "Targeting Treg Cells in Cancer Immunotherapy"; Eur J. of Immunology (2019), vol. 49, pp. 1140-1146.
Van Damme, H. et al., "Therapeutic Depletion of CCR8+ Tumor-Infiltrating Regulatory T Cells Elicits Antitumor Immunity and Synergizes with Anti-PD-1 Therapy"; J. for ImmunoTherapy of Cancer (2021); vol. 9:2, pp. e001749 (16 pgss.).
Villarreal, D. O. et al., "Targeting CCR8 Induces Protective Antitumor Immunity and Enhances Vaccine-Induced Responses in Colon Cancer"; Cancer Research (2018); vol. 78:18; 15 pgs.
Wang, L. et al. "Connecting Blood and Intratumoral Treg Cell Activity in Predicting Future Relapse in Breast Cancer"; Nature Immunology (2019); 41 pgs.
Whiteside, S. K. et al, "CCR8 Marks Highly Suppressive Treg Cells Within Tumours but is Dispensable for Their Accumulation and Suppressive Function"; Immunology (2021); vol. 163, pp. 512-520.
Lan, R. et al. "Highly Selective Anti-CCR8 Antibody?Mediated Depletion of Regulatory T Cells Leads to Potent Antitumor Activity Alone and in Combination with Anti?PD-1 in Preclinical Models"; Poster #6694 (2020), Bristol Myers Squibb, Redwood City, CA USA.
Depis, F. et al. "Preclinical Evaluation of JTX-1811, an Anti-CCR8 Antibody with Enhanced ADCC Activity, For Preferential Depletion of Tumor-infiltrating Regulatory T cells"; ASCO (2017). Abstract #4532, Jounce Therapeutics, Inc., Cambridge, MA USA.

* cited by examiner

*Primary Examiner* — Aurora M Fontainhas
*Assistant Examiner* — Jennifer Ann Benavides
(74) *Attorney, Agent, or Firm* — Fox Rothschild LLP

(57) ABSTRACT

The present disclosure provides anti-CCR8 antibodies, including compositions and methods of using such antibodies.

6 Claims, 5 Drawing Sheets

Specification includes a Sequence Listing.

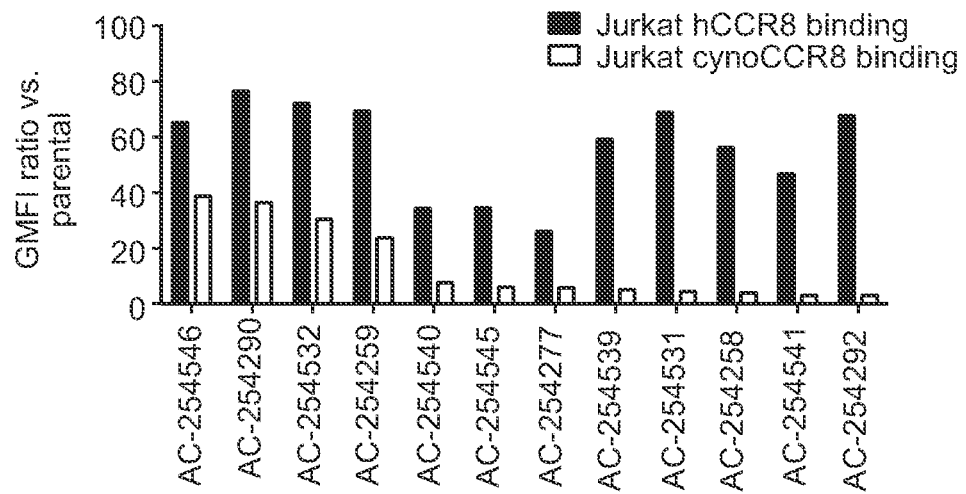
FIG. 1
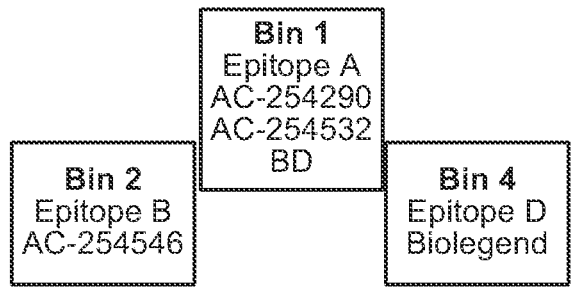
FIG. 2

ABBV-514 sequence information

>PR-1925514_LightChain huCCR8 (AC-277357) [hu IgG1/K] (VL domain underlined, constant region bold)

ETVVTQSPATLSLSPGERATLSCRASTSVITLLHWFQQKPGQAPRLLIHGASNLESRVPARFSGSGSGTDFTLTISSLEPEDFATYFCQQ
SWNDPYTFGQGTKLEIKRTVAAPSVFIFPPSDEQLKSGTASVVCLLNNFYPREAKVQWKVDNALQSGNSQESVTEQDSKDSTYSL
SSTLTLSKADYEKHKVYACEVTHQGLSSPVTKSFNRGEC

>PR-1925514_HeavyChain huCCR8 (AC-277357) [hu IgG1/K] (VH domain underlined, constant region bold)

EVQLVESGGGLVQPGGSLKLSCAASGFIFSNAVMYWVRQASGKGLEWVARIKTKFNNYATYYADAVKGRFTISRDDSKNMVYLQ
MNSLKTEDTAVYYCTAGDRNKPFAYWGQGTLVTVSSASTKGPSVFPLAPSSKSTSGGTAALGCLVKDYFPEPVTVSWNSGALTS
GVHTFPAVLQSSGLYSLSSVVTVPSSSLGTQTYICNVNHKPSNTKVDKKVEPKSCDKTHTCPPCPAPELLGGPSVFLFPPKPKDTL
MISRTPEVTCVVVDVSHEDPEVKFNWYVDGVEVHNAKTKPREEQYNSTYRVVSVLTVLHQDWLNGKEYKCKVSNKALPAPIEK
TISKAKGQPREPQVYTLPPSREEMTKNQVSLTCLVKGFYPSDIAVEWESNGQPENNYKTTPPVLDSDGSFFLYSKLTVDKSRWQ
QGNVFSCSVMHEALHNHYTQKSLSLSPGK

CDR1
CDR2
CDR3
Afucosylated residue

FIG. 3

ANTI-CCR8 ANTIBODIES

1. CROSS-REFERENCE TO RELATED APPLICATION

This application claims the benefit under 35 U.S.C. § 119(e) of U.S. provisional application No. 63/226,118, filed on Jul. 27, 2021, the disclosure of which is incorporated herein by reference in its entirety.

2. REFERENCE TO A SEQUENCE LISTING

This application includes a Sequence Listing submitted electronically as an xml file named SL-ANTI-CCR8ANTIBODIES, created on Jul. 25, 2022, with a size of 17 kilobytes. The Sequence Listing is incorporated herein by reference.

3. TECHNICAL FIELD

The present application pertains to, among other things, novel anti-CCR8 antibodies and methods of making and using the same.

4. BACKGROUND

Within tumors, regulatory T cells (Tregs) are a key suppressive population known to prevent anti-tumor immune responses. An increased presence of intratumoral Tregs has been associated with poorer patient outcomes in several cancers (Shang et al, Nature Sci. Reports, 2015; Fridman et al., Nat Rev Clin Oncol. 2017; Bruni et al., Nat Rev Cancer. 2020). Chemokine receptor 8 (CCR8) is a cell surface protein uniquely expressed by intratumoral Tregs in several human cancers (Plitas et al, Immunity 2016; De Simone et al, Immunity 2016). This makes CCR8 an attractive target to mediate selective intratumoral Treg depletion via antibody-dependent cellular cytotoxicity (ADCC) to enhance anti-tumor immunity.

While Treg depletion has long been investigated, most of these treatments have limited efficacy owing to target expression on tumor-infiltrating effector T cell populations and/or Tregs outside the tumor environment. There remains a need in the art for a monoclonal antibody therapeutic that triggers the death of intratumoral immunosuppressive Tregs without depleting other key effector T cell populations in the tumor microenvironment or peripheral Tregs.

5. SUMMARY OF INVENTION

Anti-CCR8 monoclonal antibodies have been shown to mediate selective intratumoral Treg depletion via antibody-dependent cellular cytotoxicity (ADCC). Because CCR8 is preferentially expressed by tumor infiltrating Tregs and is not highly expressed in peripheral blood Tregs or by beneficial effector T cell populations, an anti-CCR8 antibody would deplete intratumoral Tregs and enhance anti-tumor immunity. While anti-CCR8 antibody monotherapy is independently effective, the specific removal of Tregs within a tumor provides an amenable environment for appropriate combination therapy approaches aimed at concurrently stimulating the anti-tumor immune response. For instance, combination with a checkpoint inhibitor like anti-PD-1 may be required to fully drive potent anti-tumor immunity upon Treg depletion.

Accordingly, the amino acid sequence for a monoclonal, humanized antibody that specifically binds CCR8 and mediates ADCC of CCR8 expressing Tregs is provided. The antibody structurally consists of a variable heavy and variable light chain comprising complementary determining regions (CDRs) that specifically bind CCR8. The antibody also includes a human heavy chain constant region comprising a fragment crystallizable region (Fc) and a light chain constant region. These structural elements, as coded by the antibody's amino acid sequence, comprise a pharmaceutical composition effective at treating solid tumors in a patient, either as a monotherapy or in combination with other therapeutics.

6. BRIEF DESCRIPTION OF THE DRAWINGS

FIG. 1 shows binding of chimeric rat/hIgG1 human CCR8 specific chimeric mAbs to Jurkat cells expressing human or cynomolgus CCR8.

FIG. 2 shows results of epitope binning experiments.

FIG. 3 shows heavy and light chain sequences of ABBV-514.

FIGS. 5A-D show ADCC reporter bioassay data for fucosylated (WT PR-1925514) vs afucosylated ABBV-514.

Figure 4A:
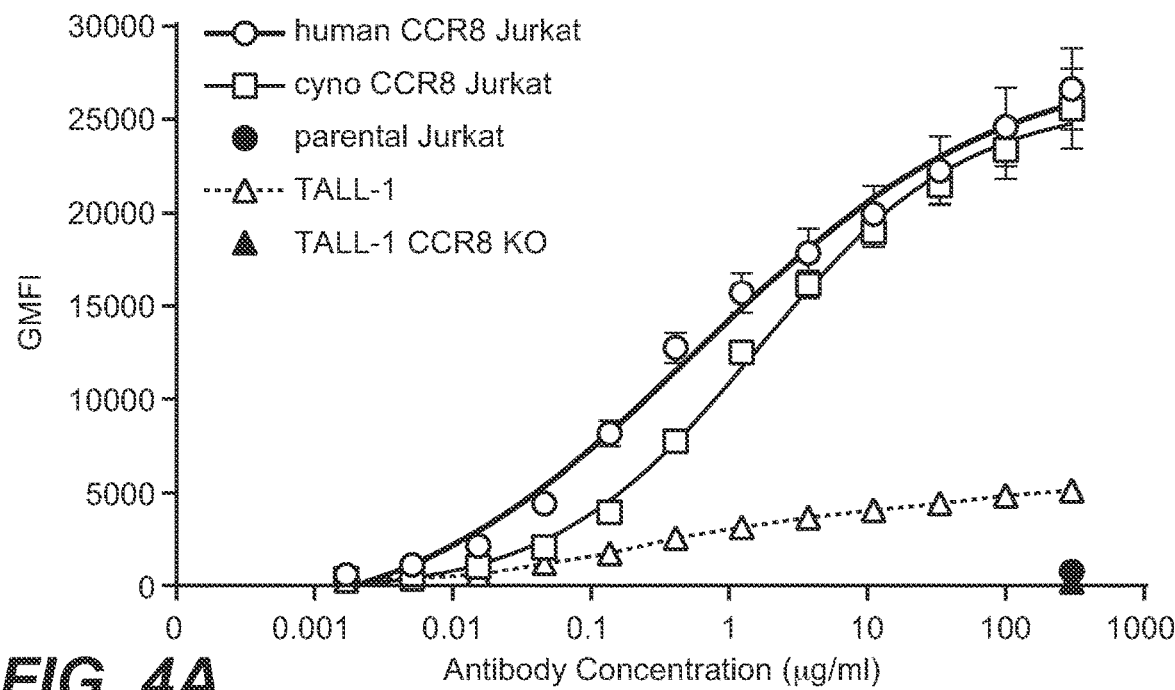
FIG. 4A shows binding dose-response curves for afucosylated ABBV-514 to TALL-1 cells expressing endogenous CCR8 or TALL-1 CCR8 knockout cells and to Jurkat parent cells or cells overexpressing human or cyno CCR8.
Figure 4B:
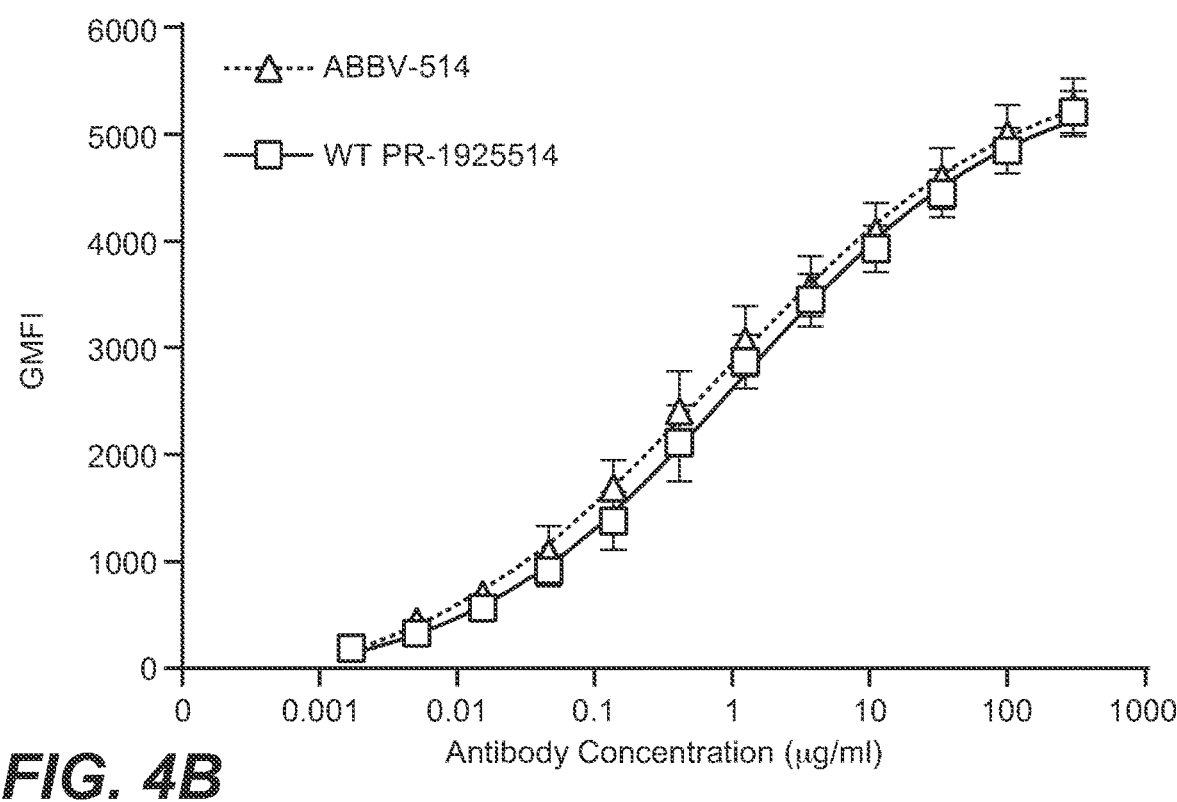
FIG. 4B shows binding of fucosylated (WT PR-1925514) vs afucosylated ABBV-514 to TALL-1 cells.
Figure 5A:
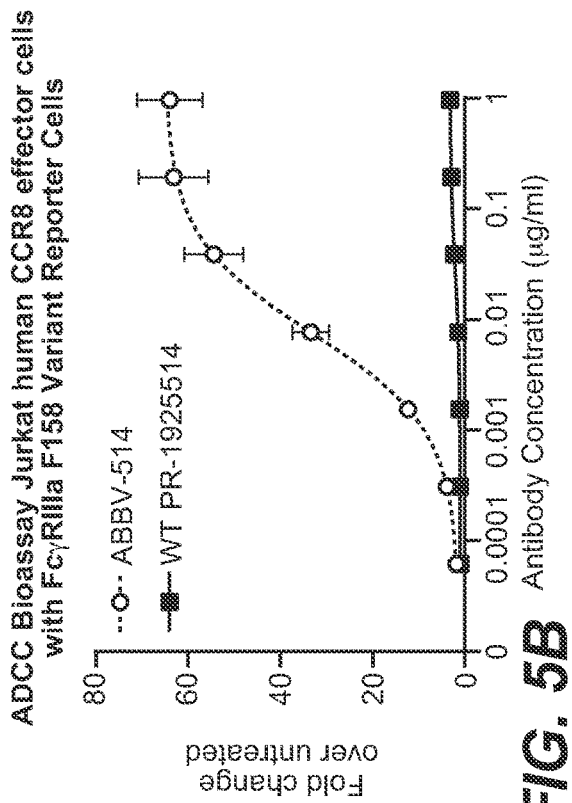
Figure 5B:
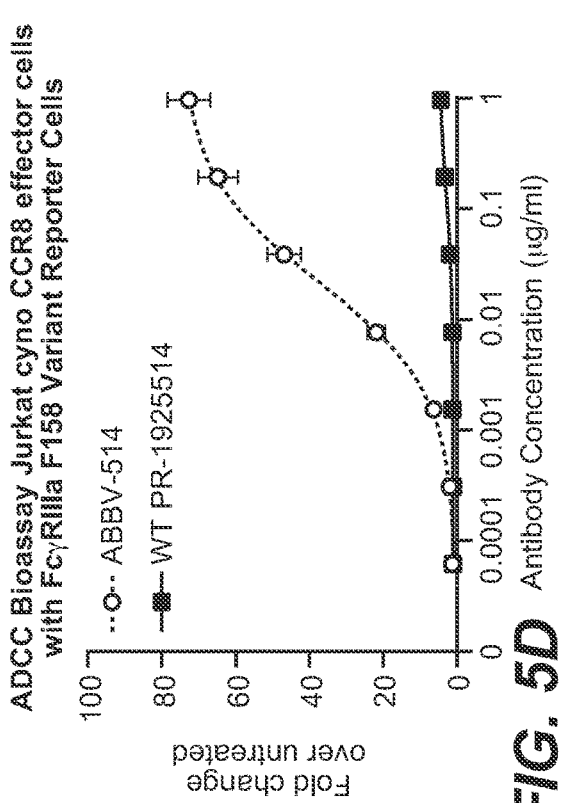
Figure 5C:
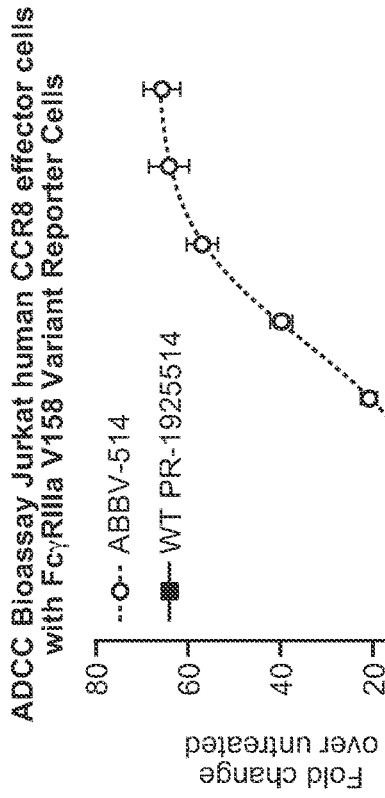
Figure 5D:
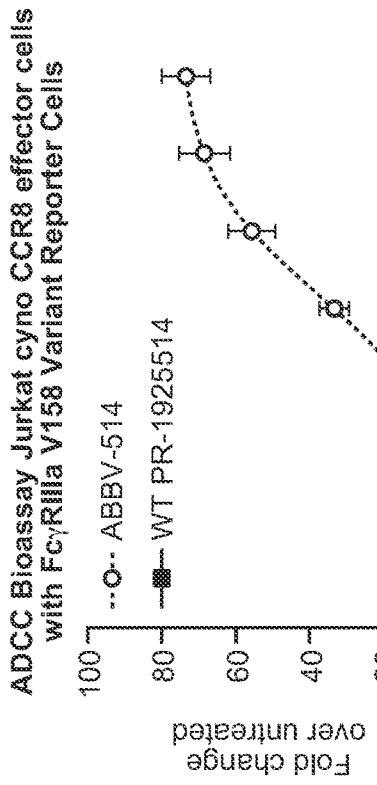
Figure 6:
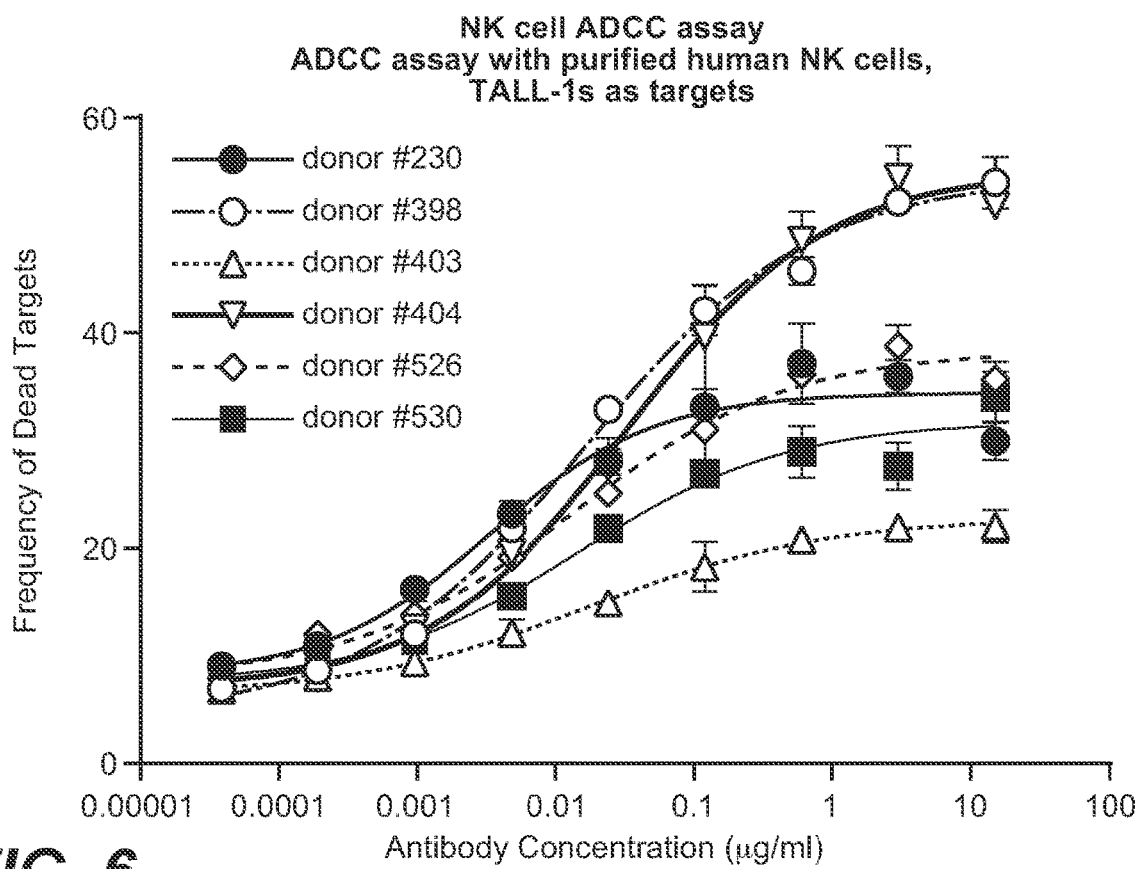

FIG. 6 shows results of an ADCC assay with purified NK effector cells and TALL-1 target cells.

Figure 7:
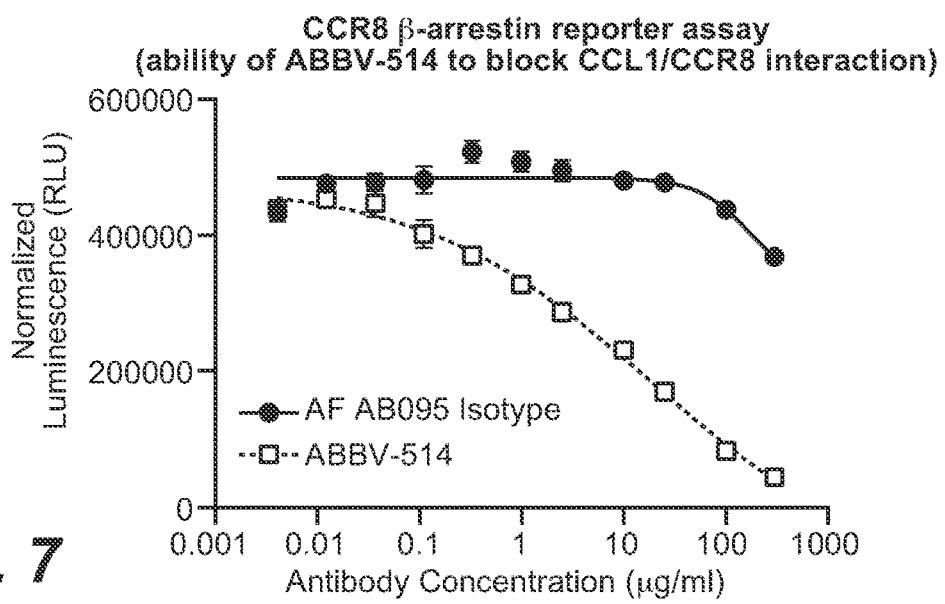

FIG. 7 show results of a CCR8 beta-arrestin reporter assay showing effect of ABBV-514 on CCL1 binding to CCR8.

7. DETAILED DESCRIPTION

Tregs are a subset of CD4+ T cells with intratumoral immunosuppressive effects. Tregs suppress the activation, proliferation, and cytokine production of CD4+ T cells and CD8+ T cells, preventing deleterious autoimmune responses. However, Tregs also suppress tumor immunity, and high intratumoral Treg levels have been associated with negative outcomes in several cancers.

CCR8 is a C-C motif chemokine receptor consisting of a seven-pass transmembrane protein that mediates chemotaxis and cell/cell interactions in the context of T-helper type 2 (Th2) lymphocyte immune responses and T cell trafficking to the skin. CCR8-deficient mice are viable, fertile, and largely normal, except that they cannot mount robust Th2 responses in certain Th2-associated preclinical models (Chensue et al., J Exp Med 5, 2001). The ligand primarily associated with CCR8 is CCL1, although CCL18 (human) and CCL8 (murine) are also ligands for this receptor.

CCR8-expressing Tregs that infiltrate tumors show a highly activated and immunosuppressive phenotype. Tumor studies in CCR8 knockout mice indicate that the loss of CCR8 expression does not influence Treg recruitment to the tumor microenvironment, activation status, or suppressive capacity (Van Damme et al., J Immunother Cancer. 9(2), 2021). Rather, CCR8 expression is a marker of highly suppressive Tregs. Therefore, depletion of CCR8-expressing Tregs provides anti-tumor benefits.

CCR8-specific surrogate antibodies mediate selective intratumoral Treg depletion via ADCC. Additionally, anti-CCR8 surrogate antibodies significantly enhance the frequency of circulating tumor-specific CD8+ effector T lymphocytes. These effects correlate with efficacy in mouse syngeneic tumor models. (Campbell et al., Cancer Research 81, 2021).

The present inventors have developed therapeutic monoclonal antibodies that specifically bind CCR8 expressed on the surface of cells, for example, intratumoral Tregs. In an embodiment, the antibody is composed of two variable chains, one heavy and one light. On each variable chain, there are three CDRs that allow the antibody to bind to CCR8. On both variable chains, there are a total of six different CDRs. Additionally, the antibody contains a human heavy chain constant region comprising a human Fc of the immunoglobulin class G1 (IgG1). The anti-CCR8 antibodies described herein can be fucosylated or afucosylated and demonstrate in vitro functionality, immunosafety, and drug-like properties.

In some embodiments, the antibody comprises an IgG Fc constant region that is afucosylated. In an embodiment, the afucosylated Fc constant region is an IgG1. Afucosylation may be carried out by techniques known in the art. See, e.g., Mol Cancer Ther (2020) 19 (5): 1102-1109) and PNAS (2013)110(14) 5404-5409. For example, production of antibodies in cell lines defective in GDP-fucose formation due to, for example, a deficiency in GDP-mannose 4,6-dehydratase; production of antibodies in cells that have decreased levels of fucosyltransferase; production of antibodies in cells that have decreased levels of GDP-fucose transporter; production of antibodies in cells that overexpress β-1,4-mannosyl-glycoprotein 4-β-N-acetylglucosaminyltransferase (GnT-III); or production of antibodies in cells that express a bacterial GDP-6-deoxy-D-lyxo-4-hexulose reductase (RMD). In an embodiment, the cells used to produce the afucosylated anti-CCR8 antibodies of the invention are CHO cells engineered to express Pseudomonas RMD. The degree of afucosylation of antibodies can be determined through techniques known in the art.

To obtain anti-CCR8 antibodies that cross-react with human and cynomolgus CCR8, the ability of mouse-human (rat/hIgG1) chimeric antibodies to bind Jurkat cells overexpressing either human or cynomolgus CCR8 was evaluated. Results were analyzed via flow cytometry as carried out by techniques known in the art. As a result, the final anti-CCR8 antibody cross-reacts with human and cynomolgus CCR8 and mediates ADCC in both species, but does not bind mouse, rat, or rabbit CCR8.

In certain embodiments, an afucosylated antibody of the invention has higher affinity for activating receptors for IgG, as well as enhanced activity in purified natural killer cell or peripheral blood mononuclear cell (PBMC) ADCC assays compared to a fucosylated form of that antibody. The ADCC activity of anti-CCR8 antibodies can be demonstrated using ADCC bioassay techniques known in the art. For example, in human FcγRIIIa V158 or F158 allelic variant reporter lines cocultured with human or cynomolgus CCR8-expressing Jurkat cells, anti-CCR8 antibodies triggered ADCC as measured via luminescence induction using techniques know in the art.

Additionally, the antibodies described herein interfere with the efficacy of other naturally occurring ligands, like CCL1, that also bind CCR8, but only at substantially higher EC50s than for binding or ADCC activity. This testing was carried out by techniques know in the art, for example via beta-arrestin reporter assays.

As used herein, the term "antibody" (Ab) refers to an immunoglobulin molecule that specifically binds to a particular antigen, e.g., CCR8. The anti-CCR8 antibodies of the disclosure bind to human CCR8 on Tregs and thereby modulate the immune system. Anti-CCR8 antibodies of the disclosure comprise complementarity determining regions (CDRs), also known as hypervariable regions, in both the light chain and the heavy chain variable domains. The more highly conserved portions of variable domains are called the framework (FR). As is known in the art, the amino acid position/boundary delineating a hypervariable region of an antibody can vary, depending on the context and the various definitions known in the art. Some positions within a variable domain may be viewed as hybrid hypervariable positions in that these positions can be deemed to be within a hypervariable region under one set of criteria while being deemed to be outside a hypervariable region under a different set of criteria. One or more of these positions can also be found in extended hypervariable regions. The disclosure provides antibodies comprising modifications in these hybrid hypervariable positions. The variable domains of native heavy and light chains each comprise four FR regions, largely by adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the target binding site of antibodies. See Kabat et al., Sequences of Proteins of Immunological Interest (National Institute of Health, Bethesda, Md. 1987).

The antibodies of the disclosure may be polyclonal, monoclonal, genetically engineered, and/or otherwise modified in nature, including but not limited to chimeric antibodies, humanized antibodies, human antibodies, single chain antibodies, etc. In various embodiments, the antibodies comprise all or a portion of a constant region of an antibody. In some embodiments, the constant region is an isotype selected from: IgA (e.g., IgA1 or IgA2), IgD, IgE, IgG (e.g., IgG1, IgG2, IgG3 or IgG4), and IgM. In specific embodiments, the anti-CCR8 antibodies described herein comprise an IgG1. In other embodiments, the anti-CCR8 antibodies comprise an IgG2. In yet other embodiments, the anti-CCR8 antibodies comprise an IgG4. As used herein, the "constant region" of an antibody includes the natural constant region, allotypes or variants.

The light constant region of an anti-CCR8 antibody may be a kappa (κ) light region or a lambda (λ) region. A λ light region can be any one of the known subtypes, e.g., λ1, λ2, λ3, or λ4. In some embodiments, an anti-CCR8 antibody comprises a kappa (κ) light region.

The term "monoclonal antibody" as used herein is not limited to antibodies produced through hybridoma technology. A monoclonal antibody is derived from a single clone, including any eukaryotic, prokaryotic, or phage clone, by any means available or known in the art. Monoclonal antibodies useful with the present disclosure can be prepared using a wide variety of techniques known in the art including the use of hybridoma, recombinant, and phage display technologies, or a combination thereof.

The term "chimeric" antibody as used herein refers to an antibody having variable sequences derived from a non-human immunoglobulin, such as a rat or a mouse antibody, and human immunoglobulin constant regions, typically chosen from a human immunoglobulin template.

"Humanized" forms of non-human (e.g., murine) antibodies comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody can also comprise at least a portion of an immunoglobulin constant region (Fc), typically that of a human immunoglobulin consensus sequence.

"Human antibodies" include antibodies having the amino acid sequence of a human immunoglobulin and include antibodies isolated from human immunoglobulin libraries or from animals transgenic for one or more human immunoglobulins and that do not express endogenous functional immunoglobulins. Human antibodies can be made by a variety of methods known in the art including phage display methods using antibody libraries derived from human immunoglobulin sequences.

Anti-CCR8 antibodies of the disclosure include full-length (intact) antibody molecules.

The anti-CCR8 antibodies may be antibodies whose sequences have been modified to alter at least one constant region-mediated biological effector function. For example, the anti-CCR8 antibodies described herein include antibodies that have been modified to acquire or improve at least one constant region-mediated biological effector function relative to an unmodified antibody, e.g., to enhance FcγR interactions (See, e.g., US Patent Appl. No. 2006/0134709) or to enhance the antibody's ability to mediate ADCC. For example, an anti-CCR8 antibody of the disclosure can have a constant region that binds FcγRI, FcγRIIA, FcγRIIB, FcγRIIIA and/or FcγRIIIB with greater affinity than the corresponding unmodified constant region. An anti-CCR8 antibody of the disclosure can be one that has a modified Fc region and mediates an enhanced ADCC response, wherein the ADCC response is enhanced with respect to an antibody having the same variable regions (i.e., VH and VL) and a wild type IgG1 Fc region (i.e., wild type CL, CH1 CH2, and CH3). Fc modifications able to enhance ADCC, such as amino acid sequence mutations, are known in the art, and can include the following sets of mutations: S239D/I332E; F243L/R292P/Y300L/V305I/P396L; S239D/I332E/A330L; and S298A/E333A/K334A.

Anti-CCR8 antibodies that comprise a human IgG4 constant region can comprise the S228P mutation, which has been reported to prevent Fab arm exchange. See, e.g., Silva, JP et al. Journal of Biological Chemistry, 290(9), 5462-5469 (2015).

In some embodiments, the anti-CCR8 antibodies include modifications that increase or decrease their binding affinities to the fetal Fc receptor, FcRn, for example, by mutating the immunoglobulin constant region segment at particular regions involved in FcRn interactions. In particular embodiments, an anti-CCR8 antibody of the IgG class is mutated such that at least one of amino acid residues 250, 314, and 428 of the heavy chain constant region is substituted alone, or in any combinations thereof. For position 250, the substituting amino acid residue can be any amino acid residue other than threonine, including, but not limited to, alanine, cysteine, aspartic acid, glutamic acid, phenylalanine, glycine, histidine, isoleucine, lysine, leucine, methionine, asparagine, proline, glutamine, arginine, serine, valine, tryptophan, or tyrosine. For position 314, the substituting amino acid residue can be any amino acid residue other than leucine, including, but not limited to, alanine, cysteine, aspartic acid, glutamic acid, phenylalanine, glycine, histidine, isoleucine, lysine, methionine, asparagine, proline, glutamine, arginine, serine, threonine, valine, tryptophan, or tyrosine. For position 428, the substituting amino acid residues can be any amino acid residue other than methionine, including, but not limited to, alanine, cysteine, aspartic acid, glutamic acid, phenylalanine, glycine, histidine, isoleucine, lysine, leucine, asparagine, proline, glutamine, arginine, serine, threonine, valine, tryptophan, or tyrosine. An exemplary substitution known to modify Fc effector function is the Fc substitution M428L, which can occur in combination with the Fc substitution T250Q. Additional specific combinations of suitable amino acid substitutions are identified in Table 1 of U.S. Pat. No. 7,217,797. Such mutations increase binding to FcRn, which protects the antibody from degradation and increases its half-life.

Anti-CCR8 antibodies with high affinity for human CCR8 may be desirable for therapeutic and diagnostic uses. Accordingly, the present disclosure contemplates antibodies having a high binding affinity to human CCR8. In specific embodiments, the anti-CCR8 antibodies binds to human CCR8 with an affinity of at least about 100 nM, but may exhibit higher affinity, for example, at least about 90 nM, 80 nM, 70 nM, 60 nM, 50 nM, 40 nM, 30 nM, 25 nM, 20 nM, 15 nM, 10 nM, 7 nM, 6 nM, 5 nM, 4 nM, 3 nM, 2 nM, 1 nM, 0.1 nM, 0.01 nM, or even higher. In some embodiments, the antibodies bind human CCR8 with an affinity in the range of about 1 pM to about 10 nM, of about 100 pM to about 10 nM, about 100 pM to about 1 nM, or an affinity ranging between any of the foregoing values.

In some embodiments, the invention provides a monoclonal anti-CCR8 antibody comprising two sets of six different complementarity-determining regions (CDRs), two sets of two different variable regions, two full heavy chains, two full light chains, and a human heavy chain constant region.

In some embodiments, the antibody is a recombinant, afucosylated, humanized, IgG1 kappa monoclonal antibody that binds to chemokine receptor 8.

In an embodiment, the antibody comprises six CDRs comprising the following sequences:
CDR-H1: GFIFSNAVMY (SEQ ID NO: 1)
CDR-H2: RIKTKFNNYATYYADAVKG (SEQ ID NO: 2)
CDR-H3: GDRNKPFAY (SEQ ID NO: 3)
CDR-L1: RASTSVITLLH (SEQ ID NO: 4)
CDR-L2: GASNLES (SEQ ID NO: 5)
CDR-L3: QQSWNDPYT (SEQ ID NO: 6)

In some embodiments, the antibody of this disclosure comprises a CDR-H1 having the amino acid sequence shown as SEQ ID NO: 1, a CDR-H2 having the amino acid sequence shown as SEQ ID NO: 2; a CDR-H3 having the amino acid sequence shown as SEQ ID NO: 3, a CDR-L1 having the amino acid sequence shown as SEQ ID NO: 4, a CDR-L2 having the amino acid sequence shown as SEQ ID NO: 5; and a CDR-L3 having the amino acid sequence shown as SEQ ID NO: 6.

In some embodiments, the antibody of this disclosure comprises a heavy chain variable region comprising the amino acid sequence shown as SEQ ID NO: 7:

```
                                          (SEQ ID NO: 7)
EVQLVESGGGLVQPGGSLKL SCAASGFIFSNAVMYWVRQA

SGKGLEWVARIKTKFNNYAT YYADAVKGRFTISRDDSKNM

VYLQMNSLKTEDTAVYYCTA GDRNKPFAYWGQGTLVTVSS;
``` and a light chain variable region comprising the amino acid sequence shown as SEQ ID NO: 8:

```
                                          (SEQ ID NO: 8)
ETVVTQSPATLSLSPGERAT LSCRASTSVITLLHWFQQKP

GQAPRLLIHGASNLESRVPA RFSGSGSGTDFTLTISSLEP

EDFATYFCQQSWNDPYTFGQ GTKLEIK.
```

In some embodiments, the antibody of this disclosure comprises a heavy chain comprising the amino acid sequence shown as SEQ ID NO: 9 (constant regions are bold; the variable heavy domain is underlined; CDRs are underlinedbolditalic (disclosed as SEQ ID NOS: 1-3, respectively, in order of appearance)):

EVQLVESGGGLVQPGGSLKLSCAAS*GFIFSNAVMY*WVRQASGKGLEWVA*RIKTKFNNYATYYA*
*DAVKG*RFTISRDDSKNMVYLQMNSLKTEDTAVYYCTA*GDRNKPFAY*WGQGTLVTVSSASTKG
PSVFPLAPSSKSTSGGTAALGCLVKDYFPEPVTVSWNSGALTSGVHTFPAVLQSSGLYSLSSV
VTVPSSSLGTQTYICNVNHKPSNTKVDKKVEPKSCDKTHTCPPCPAPELLGGPSVFLFPPKP
KDTLMISRTPEVTCVVVDVSHEDPEVKFNWYVDGVEVHNAKTKPREEQYNSTYRVVSVLT
VLHQDWLNGKEYKCKVSNKALPAPIEKTISKAKGQPREPQVYTLPPSREEMTKNQVSLTC
LVKGFYPSDIAVEWESNGQPENNYKTTPPVLDSDGSFFLYSKLTVDKSRWQQGNVFSCSVM
HEALHNHYTQKSLSLSPGK

(full-length sequence disclosed as SEQ ID NO: 9) and a light chain comprising the amino acid sequence shown as SEQ ID NO: 10 (constant regions are bold; the variable light domain is underlined; CDRs are underlinedbolditalic (CDR sequences disclosed as SEQ ID NOS: 4-6, respectively, in order of appearance)):

ETVVTQSPATLSLSPGERATLSC*RASTSVITLLH*WFQQKPGQAPRLLIH*GASNLES*RVPARFSGSG
SGTDFTLTISSLEPEDFATYFC*QQSWNDPYT*FGQGTKLEIKRTVAAPSVFIFPPSDEQLKSGTASV
VCLLNNFYPREAKVQWKVDNALQSGNSQESVTEQDSKDSTYSLSSTLTLSKADYEKHKVYA
CEVTHQGLSSPVTKSFNRGEC (full-length sequence disclosed as SEQ ID NO: 10).

In an embodiment, the antibody of the disclosure comprises a light chain according to SEQ ID NO: 10, and a heavy chain having the C-terminal lysine truncated, for example, a heavy chain according to SEQ ID NO: 9 with the C-terminal lysine truncated:

EVQLVESGGGLVQPGGSLKLSCAAS*GFIFSNAVMY*WVRQASGKGLEWVA*RIKTKFNNYATYYA*
*DAVKG*RFTISRDDSKNMVYLQMNSLKTEDTAVYYCTA*GDRNKPFAY*WGQGTLVTVSSASTKG
PSVFPLAPSSKSTSGGTAALGCLVKDYFPEPVTVSWNSGALTSGVHTFPAVLQSSGLYSLSSV
VTVPSSSLGTQTYICNVNHKPSNTKVDKKVEPKSCDKTHTCPPCPAPELLGGPSVFLFPPKP
KDTLMISRTPEVTCVVVDVSHEDPEVKFNWYVDGVEVHNAKTKPREEQYNSTYRVVSVLT
VLHQDWLNGKEYKCKVSNKALPAPIEKTISKAKGQPREPQVYTLPPSREEMTKNQVSLTC
LVKGFYPSDIAVEWESNGQPENNYKTTPPVLDSDGSFFLYSKLTVDKSRWQQGNVFSCSVM
HEALHNHYTQKSLSLSPG

(terminal lysine truncated sequence disclosed as SEQ ID NO: 11)

In one embodiment, the heavy chain of the antibody of this disclosure is encoded by the following nucleotide sequence (full-length sequence disclosed as SEQ ID NO: 12):

*ATGGAATTCGGCCTGAGCTGGCTGTTCCTGGTGGCCATCCTGAAGGGCGTGCAGTGCGAAGTCC*
AGCTGGTTGAATCTGGCGGAGGACTGGTTCAGCCTGGCGGATCTCTGAAGCTGTCTTGTGCC
GCCAGCGGCTTCATCTTCAGCAACGCCGTGATGTACTGGGTCCGACAGGCCTCTGGCAAAGG
CCTGGAATGGGTCGCCAGAATCAAGACCAAGTTCAACAACTACGCCACCTACTACGCCGAC
GCCGTGAAGGGCAGATTCACCATCAGCAGGGACGACAGCAAGAACATGGTGTACCTGCAGA

-continued
```
TGAACAGCCTGAAAACCGAGGACACCGCCGTGTACTACTGCACAGCCGGCGACAGAAACAA

GCCCTTTGCCTATTGGGGCCAGGGCACCCTGGTTACCGTTAGCTCTGCCTCCACCAAGGGC

CCATCGGTCTTCCCCCTGGCACCCTCCTCCAAGAGCACCTCTGGGGGCACAGCGGCCC

TGGGCTGCCTGGTCAAGGACTACTTCCCCGAACCGGTGACGGTGTCGTGGAACTCAGG

CGCCCTGACCAGCGGCGTGCACACCTTCCCGGCTGTCCTACAGTCCTCAGGACTCTAC

TCCCTCAGCAGCGTGGTGACCGTGCCCTCCAGCAGCTTGGGCACCCAGACCTACATCT

GCAACGTGAATCACAAGCCCAGCAACACCAAGGTGGACAAGAAAGTTGAGCCCAAATC

TTGTGACAAAACTCACACATGCCCACCGTGCCCAGCACCTGAACTCCTGGGGGGACCG

TCAGTCTTCCTCTTCCCCCCAAAACCCAAGGACACCCTCATGATCTCCCGGACCCCTGA

GGTCACATGCGTGGTGGTGGACGTGAGCCACGAAGACCCTGAGGTCAAGTTCAACTGG

TACGTGGACGGCGTGGAGGTGCATAATGCCAAGACAAAGCCGCGGGAGGAGCAGTAC

AACAGCACGTACCGTGTGGTCAGCGTCCTCACCGTCCTGCACCAGGACTGGCTGAATG

GCAAGGAGTACAAGTGCAAGGTCTCCAACAAAGCCCTCCCAGCCCCCATCGAGAAAAC

CATCTCCAAAGCCAAAGGGCAGCCCCGAGAACCACAGGTGTACACCCTGCCCCCATCC

CGGGAGGAGATGACCAAGAACCAGGTCAGCCTGACCTGCCTGGTCAAAGGCTTCTATC

CCAGCGACATCGCCGTGGAGTGGGAGAGCAATGGGCAGCCGGAGAACAACTACAAGA

CCACGCCTCCCGTGCTGGACTCCGACGGCTCCTTCTTCCTCTACAGCAAGCTCACCGT

GGACAAGAGCAGGTGGCAGCAGGGGAACGTCTTCTCATGCTCCGTGATGCATGAGGCT

CTGCACAACCACTACACGCAGAAGAGCCTCTCCCTGTCTCCGGGCAAATGA
```

Secretion signal peptide in italics; includes final stop codon (TGA); constant region is bold; CDRs are underlined.

In one embodiment, the light chain of the antibody of this disclosure is encoded by the following nucleotide sequence (full-length sequence disclosed as SEQ ID NO: 13):

```
ATGGACATGCGGGTGCCCGCCCAGCTGCTGGGACTTCTGCTGCTGTGGTTCCCCGGCAGCAGAT

GCGAGACAGTGGTCACACAGTCTCCCGCCACACTGTCACTGTCTCCAGGCGAAAGAGCCAC

ACTGAGCTGTAGAGCCAGCACCAGCGTGATCACACTGCTGCACTGGTTCCAGCAGAAGCCTG

GACAGGCTCCCAGACTGCTGATTCACGGCGCCAGCAACCTGGAAAGCAGAGTGCCTGCCAG

ATTTTCCGGCAGCGGCTCTGGCACCGATTTCACCCTGACCATAAGCAGCCTGGAACCTGAGG

ACTTCGCCACCTACTTTTGCCAGCAGAGCTGGAACGACCCCTACACCTTTGGCCAGGGCACC

AAGCTGGAAATCAAGCGAACTGTGGCTGCACCATCTGTCTTCATCTTCCCGCCATCTGA

TGAGCAGTTGAAATCTGGAACTGCCTCTGTTGTGTGCCTGCTGAATAACTTCTATCCCA

GAGAGGCCAAAGTACAGTGGAAGGTGGATAACGCCCTCCAATCGGGTAACTCCCAGGA

GAGTGTCACAGAGCAGGACAGCAAGGACAGCACCTACAGCCTCAGCAGCACCCTGACG

CTGAGCAAAGCAGACTACGAGAAACACAAAGTCTACGCCTGCGAAGTCACCCATCAGG

GCCTGAGCTCGCCCGTCACAAAGAGCTTCAACAGGGGAGAGTGTTAG
```

Secretion signal peptide in italics; includes final stop codon (TAG); constant region is bold; CDRs are underlined.

In some embodiments, the antibody comprises a human heavy chain constant region comprising human CH1, human hinge, human CH2, and human CH3 domain. In some embodiments, the encoded heavy chain constant region comprises an Fc portion, wherein the Fc portion is a human IgG1, IgG2, IgG3, IgG4, or IgM isotype. In an embodiment, the Fc is an IgG1, and the allotype is z non a. In an embodiment, the light chain is a kappa light chain.

In some embodiments, the antibody comprises an IgG1 Fc constant region that is afucosylated. Afucosylation may be carried out by techniques know in the art. For example, production of antibodies in cell lines defective in GDP-fucose formation due to, for example, a deficiency in GDP-mannose 4,6-dehydratase; production of antibodies in cells that have decreased levels of fucosyltransferase; production of antibodies in cells that have decreased levels of GDP-fucose transporter; production of antibodies in cells that overexpress β-1,4-mannosyl-glycoprotein 4-β-N-acetylglucosaminyltransferase (GnT-III); or production of antibodies in cells that express a bacterial GDP-6-deoxy-D-lyxo-4-hexulose reductase (RMD). The cells used to produce the afucosylated anti-CCR8 antibodies of the invention are CHO cells engineered to express Pseudomonas RMD. The degree of afucosylation of antibodies can be determined through techniques known in the art. Typically, the antibody is 70% or more, 80% or more, 90% or more, or about 99%, or about 100% afucosylated. Preferably, the degree of afucosylation is equal to or greater than 80%. In some embodiments, the antibody is 70% or more, 80% or more, 90% or more, or about 100% afucosylated at position ASN-300 (EU: ASN-297). Afucosulyation can be determined via hydrophilic interaction chromatography (HILIC) assay techniques, in which the degree of afucosylation is determined by polarity-dependent separation of the fragmented antibodies.

In an embodiment, the total afucosylated glycan species is determined by analysis of released N-linked glycans by HILIC with fluorescent detection. The glycans are released using peptide N-glycosidase F (PNGaseF) and subsequently labeled with a fluorescent tag. Fluorescently labeled N-linked glycans are analyzed by HILIC with fluorescence detection. The percent afucosylated glycan species is determined based on the sum of the peak areas of all afucosylated glycan peaks relative to the total peak area of all glycan peaks in the chromatogram. All peaks with a relative abundance of 0.5% or greater are included in the determination of percent afucosylated glycan species.

7.1. Polynucleotides Encoding the Anti-CCR8 Antibodies, Expression Systems and Methods of Making the Antibodies The present disclosure encompasses polynucleotide molecules encoding immunoglobulin light and heavy chain genes for anti-CCR8 antibodies, vectors comprising such polynucleotides, and host cells capable of producing the anti-CCR8 antibodies of the disclosure.

An anti-CCR8 antibody of the disclosure can be prepared by recombinant expression of immunoglobulin light and heavy chain genes in a host cell. To express an antibody recombinantly, a host cell is transfected with one or more recombinant expression vectors carrying DNA fragments encoding the immunoglobulin light and heavy chains of the antibody such that the light and heavy chains are expressed in the host cell and, optionally, secreted into the medium in which the host cells are cultured, from which medium the antibodies can be recovered.

To generate polynucleotides encoding such anti-CCR8 antibodies, DNA fragments encoding the light and heavy chain variable regions are first obtained. These DNAs can be obtained by amplification and modification of germline DNA or cDNA encoding light and heavy chain variable sequences, for example using the polymerase chain reaction (PCR).

Once DNA fragments encoding anti-CCR8 antibody-related VH and VL segments are obtained, these DNA fragments can be further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker. The term "operatively linked," as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (CH1, CH2, CH3 and, optionally, CH4). The sequences of human heavy chain constant region genes are known in the art (See, e.g., Kabat, E.A., et al., 1991, Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region, but in certain embodiments is an IgG1 or IgG4. For a Fab fragment heavy chain gene, the VH-encoding DNA can be operatively linked to another DNA molecule encoding only the heavy chain CH1 constant region.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (See, e.g., Kabat, et al., 1991, Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region, but in certain embodiments is a kappa constant region.

To express the anti-CCR8 antibodies of the disclosure, DNAs encoding partial or full-length light and heavy chains, obtained as described above, are inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vectors or, more typically, both genes are inserted into the same expression vector.

The antibody genes are inserted into the expression vector by standard methods (e.g., ligation of complementary restriction sites on the antibody gene fragment and vector, or blunt end ligation if no restriction sites are present). Prior to insertion of the anti-CCR8 antibody-related light or heavy chain sequences, the expression vector can already carry antibody constant region sequences. For example, one approach to converting the anti-CCR8 monoclonal antibody-related VH and VL sequences to full-length antibody genes is to insert them into expression vectors already encoding heavy chain constant and light chain constant regions, respectively, such that the VH segment is operatively linked to the CH segment(s) within the vector and the VL segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the disclosure carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes.

In addition to the antibody chain genes and regulatory sequences, the recombinant expression vectors of the disclosure can carry additional sequences, such as sequences that regulate replication of the vector in host cells (e.g., origins of replication) and selectable marker genes. The selectable marker gene facilitates selection of host cells into which the vector has been introduced. For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, lipofection, calcium-phosphate precipitation, DEAE-dextran transfection and the like.

It is possible to express the antibodies of the disclosure in either prokaryotic or eukaryotic host cells. In certain embodiments, expression of antibodies is performed in eukaryotic cells, e.g., mammalian host cells, of optimal secretion of a properly folded and immunologically active antibody. Exemplary mammalian host cells for expressing the recombinant antibodies of the disclosure include Chinese Hamster Ovary (CHO cells) (including DHFR-CHO cells, described in Urlaub and Chasin, 1980, Proc. Natl. Acad. Sci. USA 77:4216-4220, used with a DHFR selectable marker, e.g., as described in Kaufman and Sharp, 1982, Mol. Biol. 159:601-621), NSO myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or secretion of the antibody into the culture medium in which the host cells are grown. Antibodies can be recovered from the culture medium using standard protein purification methods. Host cells can also be used to produce portions of intact antibodies, such as Fab fragments or scFv molecules. It is understood that variations on the above procedure are within the scope of the present disclosure. For example, it can be desirable to transfect a host cell with DNA encoding either the light chain or the heavy chain (but not both) of an anti-CCR8 antibody of this disclosure.

Recombinant DNA technology can also be used to remove some or all of the DNA encoding either or both of the light and heavy chains that is not necessary for binding to human CCR8. The molecules expressed from such truncated DNA molecules are also encompassed by the antibodies of the disclosure.

For recombinant expression of an anti-CCR8 antibody of the disclosure, the host cell can be co-transfected with two expression vectors of the disclosure, the first vector encoding a heavy chain derived polypeptide and the second vector encoding a light chain derived polypeptide. The two vectors can contain identical selectable markers, or they can each contain a separate selectable marker. Alternatively, a single vector can be used which encodes both heavy and light chain polypeptides.

Once a polynucleotide encoding one or more portions of an anti-CCR8 antibody has been obtained, further alterations or mutations can be introduced into the coding sequence, for example to generate polynucleotides encoding antibodies with different CDR sequences, antibodies with reduced affinity to the Fc receptor, or antibodies of different subclasses.

The anti-CCR8 antibodies of the disclosure can also be produced by chemical synthesis or by using a cell-free platform.

7.2. Purification of Anti-CCR8 Antibodies

Once a polypeptide of the disclosure has been produced by recombinant expression, it can be purified by any method known in the art for purification of a protein. Once isolated, an anti-CCR8 antibody can be further purified.

7.3. Compositions

The antibodies of this disclosure may be provided as a composition suitable for administration to a subject. In some embodiments, the antibody composition is a pharmaceutical composition, comprising an antibody of this disclosure and a pharmaceutically acceptable carrier.

In an embodiment, a pharmaceutical composition comprising a plurality of anti-CCR8 antibodies and a pharmaceutically acceptable carrier is provided. In an embodiment, the plurality of anti-CCR8 antibody of the pharmaceutical composition is afucosylated. Typically, the plurality of antibodies is 70% or more, 80% or more, 90% or more, or about 99%, or about 100% afucosylated. Preferably, the degree of afucosylation is equal to or greater than 90%. In some embodiments, the plurality of antibodies is 70% or more, 80% or more, 90% or more, or about 100% afucosylated at position ASN-300 (EU: ASN-297). The degree of afucosylation of antibodies can be determined through techniques known in the art. Afucosylation can be determined via hydrophilic interaction chromatography (HILIC) assay techniques, in which the degree of afucosylation is determined by polarity-dependent separation of the fragmented antibodies. In an embodiment, the total afucosylated glycan species is determined by analysis of released N-linked glycans by HILIC with fluorescent detection. The glycans are released using peptide N-glycosidase F (PNGaseF) and subsequently labeled with a fluorescent tag. Fluorescently labeled N-linked glycans are analyzed by HILIC with fluorescence detection. The percent afucosylated glycan species is determined based on the sum of the peak areas of all afucosylated glycan peaks relative to the total peak area of all glycan peaks in the chromatogram. All peaks with a relative abundance of 0.5% or greater are included in the determination of percent afucosylated glycan species.

7.4. Summary of Properties of Subject Antibodies

Properties of subject antibodies, exemplified by but not limited to ABBV-514, include the following:

High affinity binding to CCR8, e.g., FACS binding mean $EC_{50}$ of 2 µg/mL or lower, 1 µg/mL or lower, from 0.3 through 0.7 µg/mL, 0.4 through 0.6 µg/mL, about 0.5 µg/mL, or 0.55 µg/mL determined with endogenously expressed CCR8 on TALL-1 cells (Human adult T-ALL; RRID: CVCL 1736); or FACS binding mean $EC_{50}$ to human CCR8 overexpressed on Jurkat cells of 2 µg/mL or lower, 1 µg/mL or lower, from 0.3 through 0.8 µg/mL, 0.4 through 0.7 µg/mL, about 0.5 µg/mL, or 0.6 µg/mL; or FACS binding mean $EC_{50}$ to CCR8 expressed on CD45RA low Tregs in human blood of 2 µg/mL or lower, 1 µg/mL or lower, from 0.2 through 0.6 µg/mL, 0.3 through 0.5 µg/mL, about 0.5 µg/mL, or 0.48 µg/mL.

High specificity binding to human CCR8, e.g., no specific FACS binding to TALL-1 CCR8 knockout cells or parental Jurkat cells.

Cross reactivity with cynomolgus CCR8, e.g., FACS binding mean $EC_{50}$ to cyno CCR8 overexpressed on Jurkat cells of 5 µg/mL or lower, 3 µg/mL or lower, 2 µg/mL or lower, approximately 1.5 µg/mL, or 1.82 µg/mL; or to CCR8 expressed on CD45RA low Tregs in cyno blood of 5 µg/mL or lower, 3 µg/mL or lower, 2 µg/mL or lower, approximately 1.5 µg/mL, or 1.62 µg/mL.

Poor ability to block CCL1/CCR8 interaction, e.g., $EC_{50}$ of CCL1/CCR8 blocking activity at least 30× higher, at least 40× higher, between 30× and 70× higher, at least 50× higher, or at least about 50× higher than $EC_{50}$ of binding to human CCR8.

Enhanced ability to induce ADCC with respect to an antibody with the same variable regions and a wild type, fucosylated IgG1.

Enhanced binding to Fcγ receptors with respect to an antibody with the same variable regions and a wild type, fucosylated IgG1.

Good immunosafety determined by cytokine release assay.

7.5. Methods of Use

In embodiments, the methods described herein involve treating patients who have solid tumors with the anti-CCR8 antibodies of the invention. In embodiments, a composition comprising anti-CCR8 antibodies is administered to subject in need thereof.

In the PD-1 refractory Pan02 mouse model, a combination of CCR8 and PD-1 targeting antibodies showed improved in vivo efficacy over monotherapy with either antibody. Depleting immunosuppressive CCR8+ Tregs may synergize with PD-1/PD ligand 1 (PD-L1) blockade to promote a stronger CD8+ effector T-cell response and enhance antitumor immunity. In an embodiment, the composition comprising anti-CCR8 antibodies is administered as part of combination therapy comprising administration of a PD-1 or PD-L1 targeting antibody. In an embodiment, the composition comprising anti-CCR8 antibodies is administered as a combination therapy with pembrolizumab, budigalimab, nivolumab, cemiplimab, or dostarlimab. In an embodiment, the composition comprising anti-CCR8 antibodies is administered as a combination therapy with atezolizumab, avelumab, durvalumab.

8. EXAMPLES

The following examples, which highlight certain features and properties of the exemplary embodiments of the antibodies and binding fragments described herein are provided for purpose of illustration.

8.1. Example 1: Production of Rat Hybridomas

Rats were immunized with 2 different full-length human CCR8 cDNA vectors (6 rats for each vector). Lymph node cells were isolated and fused to NSO to generate hybridomas. Following expansion, hybridoma supernatants were screened for binding to human or cynomolgus ("cyno" or "cy") CCR8 overexpressed on HEK293 cells. 46 rat/hIgG1 chimeric mAbs were expressed via high-throughput antibody production, and 21 were confirmed to bind to human CCR8 (FIG. 1). Four chimeric mAbs AC-254290, AC-254532, AC-254546, and AC-254259 were selected for full humanization based on highest cyno cross-reactivity in Jurkat CCR8 overexpressing lines.

8.2. Example 2: Epitope Mapping by Competition Binding to huCCR8

The selected chimeric antibodies were tested for binding to human CCR8 on Jurkat cells through cellular epitope mapping assays along with human CCR8 antibodies from BD Biosciences (clone 433H) and Biolegend (clone L263G8). Both commercial antibodies were reported as being generated by immunizing mice with human CCR8-transfectants, and neither are cross reactive with cyno CCR8. The antibodies were tested pairwise with cells stained with saturating concentrations of antibody 1, washed, and then stained with antibody 2 or vice versa.

mAbs AC-254290 and AC-254532 interfered with binding in either order suggesting they bind to the same epitope (Epitope A) (FIG. 2). AC-254546 shows moderate epitope binding interference with AC-254290 and AC-254532 but no evidence of binding to the same epitope; therefore AC-254546 binds to Epitope B which is unique but close to Epitope A. AC-254259 had no binding interference with any other antibody and is likely a unique epitope (Epitope C). BD Biosciences clone 433H had the same epitope binding as AC-254290 and some interference binding with AC-254532, AC-254546, and Biolegend clone L263G8, and is therefore binned with Epitope A. Based on interference data with BD Biosciences clone 433H and the other antibodies, Biolegend clone L263G8 is binned as Epitope D, which is unique but close to Epitope A but not Epitope B.

8.3. Example 3: Humanization of Rat Variable Domain/Human IgG1 Fc Chimeras

The four chimeric antibodies AC-254290, AC-254532, AC-254546, and AC-254259 were humanized by (i) identifying the rodent antibody sequence; (ii) identifying the CDRs and antibody frameworks; (iii) creating a VH-VL structural model; (iv) identifying a framework residue for back mutation, to maintain function of rodent antibody; (v) selecting human germlines with high identity, most similar CDR canonical structures, and least back mutations needed; and (iv) generating a VH/VL sequence by CDR grafting and incorporating the selected back mutations.

Four humanized antibodies were created for each selected antibody. AC-254290 required both sequence-based and structure-based approaches for humanization. Straight CDR grafting resulted in an antibody having poor binding to human CCR8 expressing Jurkat cells. Back-mutations based on a predicted rodent VH/VL structure/interface were tested. The residue triplet prior to HCDR3 was CTA, which is atypical. Position 94 (the A in CTA) is almost always an arginine (R). Two humanized versions with CTR exhibited poor binding to human CCR8 expressing Jurkat cells, with $EC_{50}$s of 3.96 and 5.61 µg/mL. In contrast, two humanized versions with CTA prior to HCDR3 (CTAGDRNKPFAY (SEQ ID NO: 14)), one of which being AC-264700, demonstrated strong binding, with $EC_{50}$s of 0.2559 and 0.2302

µg/mL, comparing favorably to the AC-254290 parent antibody ($EC_{50}$ of 0.4538 µg/mL).

The humanized antibodies were assessed for their ability to bind human or cynomolgus CCR8. $EC_{50}$s were determined by testing 8 concentrations of antibody starting at 30 µg/mL with 5× dilutions for binding to the human or cynomolgus CCR8 overexpressing Jurkat cells. Following incubation with test CCR8 antibodies, cells were washed and incubated with fluorochrome labeled secondary antibodies, washed and analyzed via flow cytometry.

AC-254259 and AC-254532 exhibited decreased binding to cynoCCR8 and high non-specific binding to HEK293 cells, respectively. AC-264711 (humanized AC-254546) and AC-264700 (humanized AC-254290) were advanced because of their superior target binding, absence of non-specific binding, and limited requirement for liability engineering.

8.4. Example 4: Liability Engineering of AC-264700

AC-264700 had DS motifs in HCDR2 and in LCDR1 at amino acids 61-62 and 27-28, respectively (kabat) which are risks for isomerization and a DP motif at amino acid positions 94-95 (kabat) in LCDR3 that made it subject to potential fragmentation. The HCDR2 DS liability was mutated to DA based on experience with previous antibodies. Removal of the DP motif disrupted binding, but fragmentation of antibodies retaining the DP motif was not manifested under stress testing. Twenty-two LCDR1 DS variant antibodies were created, and their binding properties were assessed using flow cytometry against overexpressed huCCR8 or cyCCR8 Jurkat cells. Non-specific binding to Jurkat parental cells was assessed through flow cytometry. Ten of the variant antibodies were selected for further characterization based on favorable functional and drug-like properties. Two were chosen for advancement based on their overall combination of properties, including binding, reduced self-interaction, lack of non-specificity, cyno cross reactivity, and activity in the hFcγRIIIa V variant ADCC reporter bioassay (Promega).

The candidate molecules were assessed for binding capacity using flow cytometry through known methods against overexpressed huCCR8 or cyCCR8 on the surface of Jurkat cells. The exemplary antibodies were tested for their ability to self-interact, bind to huCCR8 and cyCCR8, capacity for ADCC using the reporter bioassay, and non-specific binding to HEK293 cells. AC-277357 had superior binding capacity for both huCCR8 and cyCCR8 Jurkat cells when compared to parent and other candidate antibodies (Table 1). The AC-SINS self-interaction scores for each candidate was <1. At 100 µg/mL, non-specific binding maximums ranged from 97 to 144 GMFI. At 10 µg/mL, non-specific binding maximums ranged from 94-111 GFMI. At 1 µg/mL, non-specific binding maximums ranged from 87-102 GMFI. AC-277357 had the lowest non-specific binding maximum to HEK293 cells at 100 µg/mL, strongest binding to huCCR8 and cyCCR8 Jurkat cells, and largest fold induction of signal with both huCCR8 and cyCCR8 Jurkat target cells in the ADCC reporter bioassay. Additionally, AC-277357 had one of the lowest self-interaction scores when compared to the parent antibody.

TABLE 1

Comparison of AC-264700 Variants

| Antibody | | AC-264700 | AC-277357 | AC-277371 | AC-277483 |
|---|---|---|---|---|---|
| | | | Mutation | | |
| | | DS | D27→T | D27→G | S28→A |
| Binding to hu/cy CCR8 Jurkats | huCCR8 $EC_{50}$ (nM) | 2.33 | 1.51 | 1.87 | 2.90 |
| | cyCCR8 $EC_{50}$ (nM) | 5.27 | 2.37 | 4.83 | 5.93 |
| ADCC reporter hu/cyCCR8 expressing Jurkat target cells | huCCR8 $EC_{50}$ (nM) | 0.12 | 0.10 | 0.05 | 0.07 |
| | Max Fold Induction | 12.8 | 15.7 | 12.7 | 13.6 |
| | cyCCR8 $EC_{50}$ (nM) | 0.79 | 0.75 | 0.57 | 1.19 |
| | Max Fold Induction | 12.0 | 12.3 | 11.7 | 10.0 |

8.5. Example 5: Liability Engineering of AC-264711

AC-264711 had a NS motif at amino acids 60-61 (kabat) in the HCDR2 region, which presented a risk for deamination. Additionally, residue M100c in HCDR3 showed high levels of oxidation during stress testing.

Candidate AC-264711 variants with NS mutations to remove liabilities were tested for their capacity to self-interact, non-specifically bind to HEK293 cells, bind to huCCR8 and cyCCR8 Jurkat cells, and induce signal in the ADDC reporter bioassay with huCCR8 expressing Jurkat cells as targets. Removing the NS motif was tolerated. Twenty-nine NS variants were created, and their binding properties were assessed using flow cytometry against Jurkat parental cells and overexpressed huCCR8 or cyCCR8 Jurkat cells. Five antibodies with the best binding and drug-like property profiles were tested in the ADCC reporter bioassay and the three antibodies with the best combination of properties, AC-275889, AC-275896 and AC-275898, were advanced for M100c mutations to prevent oxidation.

Variants of AC-275889, AC-275896 and AC-275898 with M100c mutations were generated and tested in the same assays as NS mutants. Data from these assays were used to prioritize eight antibodies for drug-like property testing. AC-291774 and AC-291790 had the highest self-interaction AC-SINS scores at 8.38 and 6.75, respectively. The remaining candidates had comparable AC-SINS scores ranging from 1.73 to 2.79. AC-275896 and AC-275898 had the largest non-specific binding to HEK293 cells at 1780 and 1065, GFMI respectively. AC-291790, AC-275889, and AC-275898 had non-specific binding maximums of 335, 148, and 141, respectively. At 10 and 1 µg/mL, all candidate molecules had comparable non-specific binding maximums ranging from 61 to 67 and 57 to 60, respectively. AC-291774 and AC-291790 had the lowest non-specific binding as indicated by binding to Jurkat parental cells and hydrophobic interaction chromatography, while maintaining potent binding to huCCR8 and cyCCR8 expressing Jurkat cells and comparable $EC_{50}$s and fold induction of ADCC reporter signal with both huCCR8 and cyCCR8 expressing Jurkat cells when compared to AC-275889, AC-275896 and AC-275898 (Table 2).

TABLE 2

| In vitro assays of AC-264711 Variants | | | | | | |
|---|---|---|---|---|---|---|
| Antibody | AC Number Mutation | AC-275889 N60→A | AC-275896 S61→E | AC-275898 S61→Q | AC-291774 N60→A M106→I | AC-291790 S61→Q M106→I |
| Binding to hu/cy CCR8 Jurkats | huCCR8 $EC_{50}$ (nM) | 12.19 | 49.41 | 8.39 | 9.57 | 17.67 |
| | cyCCR8 $EC_{50}$ (nM) | 7.08 | 13.70 | 24.41 | 9.00 | 15.28 |
| ADCC huCCR8 expressing Jurkats | huCCR8 $EC_{50}$ (nM) | 0.07 | 0.15 | 0.12 | 0.19 | 0.23 |
| | Max Fold Induction | 15.6 | 14.1 | 17.0 | 16.8 | 18.6 |
| | cyCCR8 $EC_{50}$ (nM) | 0.10 | 0.41 | 0.10 | 0.30 | 0.30 |
| | Max Fold Induction | 8.7 | 7.7 | 10.7 | 10.8 | 12.7 |

8.6. Example 6: Final Candidate Antibody Selection

AC-277357, AC-277371, AC-291774 and AC-291790 were selected to be further evaluated in additional drug-like property and in vitro immunosafety experiments. To generate an afucosylated variant for characterization, cells expressing AC-277357 were transfected with a plasmid for expression of the Pseudomonas enzyme GDP-6-deoxy-D-lyxo-4-hexulose reductase (RMD), which converts an intermediate in the de novo synthesis of fucose to a dead-end product, resulting in the production of afucosylated AC-277357.

Candidate molecules were assessed for Jurkat huCCR8, Jurkat cyCCR8 and TALL-1 binding activity, hPBMC ADCC activity with TALL-1 as targets, ADCC activity in F158 effector cells with huCCR8 overexpressing Jurkat cells as targets, and V158 effector cells with huCCR8 overexpressing Jurkat cells as targets. AC-277357 (also referred to as PR-1925514), showed improved binding to endogenous levels of CCR8 expression on TALL-1 cells and the afucosylated version was more active in primary cell ADCC assays (data not shown). AC-277357/PR-1925514 binds more potently to CCR8 on human Tregs and has a better profile in cytokine release assays than AC-291774 (also referred to as PR-1928444) (data not shown). AC-277357/PR-1925514 with an afucosylated human IgG1 Fc was chosen as the lead antibody because it had the best in vitro functional and in vitro immunosafety (IVIS) profile as well as excellent drug like properties.

8.7. Example 7: Binding and Functional Potency Assays

Antibodies were screened via single point flow cytometry to assess binding to Jurkat cells lines overexpressing human or cynomolgus monkey CCR8. $EC_{50}$s were determined by testing eight concentrations of antibody starting at 30 μg/mL with 5× dilutions for binding to the Jurkat human CCR8, Jurkat cyno CCR8 and parental Jurkat cells via flow cytometry. Following incubation with test CCR8 antibodies, cells were washed and incubated with fluorochrome labeled secondary antibodies, washed and analyzed via flow cytometry.

Human FcγRIIIa V Variant Core Kit or Human FcγRIIIa F Variant Cell Propagation Model were purchased from Promega and used as directed. Jurkat target cell lines overexpressing human or cynomolgus monkey CCR8 or parental Jurkat control cells were washed once in ADCC assay buffer, diluted to 6 ×$10^6$ cells per mL in ADCC assay buffer, and plated at 25 μL per well into white walled 96-well assay plates (Costar). Antibodies were diluted at 3× final concentration in ADCC assay buffer for addition at 25 μL per well (1:5 fold 7-point dilutions ranging from 1 μg/mL to 0.000064 μg/mL were tested). Effector cells (stably expressing either the human FcγRIIIa V158 variant, the human FcγRIIIa F158 variant, or mouse FcγRIV and an NFAT response element driving expression of firefly luciferase) were thawed and added at a final effector to target ratio of 1:2.5. After incubation at 37° C., 5% CO2 for 6 hours BioGlo reagent (Promega) was mixed and added as directed and luminescence signal was measured.

8.8. Example 8: Dose Response Curves for ABBV-514

Fucosylated and afucosylated (renamed ABBV-514) versions of AC-277357/PR-1925514 were evaluated for cell binding to Jurkat cell lines overexpressing human or cyno CCR8 and to TALL-1 cells that express endogenous levels of CCR8. Cell binding was assessed through flow cytometry using similar methods discussed above. Additionally, binding was evaluated for parental Jurkat (no CCR8 expression) and CCR8 knock-out (KO) TALL-1 control lines. ABBV-514 showed binding to both human and cyno CCR8 overexpressed in Jurkat cells, but not to the parental Jurkat or CCR8 KO TALL-1 cells (FIG. 4A). ABBV-514 also bound to endogenous CCR8 on TALL-1 cells similar to that of fucosylated (WT) AC-277357/PR-1925514 (FIG. 4B).

Both fucosylated WT PR-1925514 and ABBV-514 mediate ADCC as measured by luminescence induction in a human FcγRIIIa reporter cell-based bioassay using either FcγRIIIa V158 (FIGS. 5A, 5C) or F158 (FIGS. 5B, 5D) allelic variant reporter lines cocultured with human (FIGS. 5A, 5B) or cyno (FIGS. 5C, 5D) CCR8 overexpressing Jurkat cells. The fold change in luminescence compared to untreated cocultures is presented as the mean ±SEM of 2-5 independent experiments. ABBV-514 exhibited increased ADCC activity as indicated by the ADCC reporter bioassay compared to fucosylated WT PR-1925514. For purposes of comparison to concentrations expressed in μg/mL, a concentration of 1 μg/mL of antibody equals 6.76 nM.

8.9. Example 9: Primary Cell ADCC Assay Data for ABBV-514

The activity of ABBV-514 was further evaluated in a cell cytotoxicity-based ADCC assay using TALL-1 cells as targets and human primary NK cells as effectors. Six donor sources of NK cells were used to as target cells and cell death of TALL-1 target cells was assessed via flow cytometry using similar methods discussed above. ABBV-514 mediated ADCC of CCR8 expressing TALL-1 cells by all six donor NK cell specimens (FIG. 6). ADCC activity in human whole blood cultures was assessed via flow cytometry using adapted procedures described above. After 48 hours, a culture of human whole blood with ABBV-514 was analyzed to assess the fraction of CD45RA low Tregs of total CD45+ hematopoietic cells. CD45RA low Tregs includes live CD45+, CD3+, CD4+, CD25+, CD127 low, Foxp3+, CD45RA low cells, which are known to be enriched in CCR8 expression. Human whole blood cell data from 11 healthy donors were assessed. In each donor, ABBV-514 decreased the amount percentage of CD45RA low Tregs of live CD45+ cells (data not shown).

8.10. Example 10: Assessment of CCL1 Ligand Blockade by ABBV-514

A CCR8 beta-arrestin reporter assay was used to determine whether ABBV-514 blocked the interaction of CCR8 with its ligand, CCL1 (FIG. 7). Inhibition of CCL1-mediated reporter activation in the presence of ABBV-514 was observed only at substantially higher concentrations of antibody than those at which binding or ADCC activity was observed, with an $EC_{50}$ of CCL1 blockade observed at 23.1 µg/mL.

9. EXEMPLARY EMBODIMENTS

While various specific embodiments have been illustrated and described, and some are represented below, it will be appreciated that various changes can be made without departing from the spirit and scope of the inventions(s).

1. An anti-CCR8 antibody which comprises (i) a VH chain comprising three CDRs; and (ii) a VL chain comprising three CDRs, wherein:
   VH CDR#1 is GFIFSNAVMY (SEQ ID NO:1);
   VH CDR#2 is RIKTKFNNYATYYADAVKG (SEQ ID NO:2);
   VH CDR#3 is GDRNKPFAY (SEQ ID NO:3);
   VL CDR#1 is RASTSVITLLH (SEQ ID NO:4);
   VL CDR#2 is GASNLES (SEQ ID NO:5); and
   VL CDR#3 is QQSWNDPYT (SEQ ID NO:6).
2. The anti-CCR8 antibody of embodiment 1, wherein the antibody comprises the amino acid sequence CTA immediately prior to VH CDR#3, whereby the antibody comprises the amino acid sequence CTAGDRNKPFAY (SEQ ID NO: 14).
3. The anti-CCR8 antibody of embodiment 1, wherein the antibody comprises a heavy chain variable region comprising the amino acid sequence set forth as SEQ ID NO: 7 and a light chain variable region comprising the amino acid sequence set forth as SEQ ID NO: 8.
4. The anti-CCR8 antibody of embodiment 1, wherein the antibody comprises a heavy chain comprising the amino acid sequence set forth as SEQ ID NO: 9 and a light chain comprising the amino acid sequence set forth as SEQ ID NO: 10
5. The anti-CCR8 antibody according to embodiment 3, wherein the antibody is afucosylated.
6. A composition comprising a plurality of the anti-CCR8 antibodies of embodiment 1.
7. The composition of embodiment 6, wherein greater than 80% of the anti-CCR8 antibodies in the composition are afucosylated.
8. The anti-CCR8 antibody of embodiment 1, which is an IgG.
9. The anti-CCR8 antibody of embodiment 1, wherein the antibody comprises a human heavy chain constant region comprising an Fc portion, where the Fc portion is a human IgG1, IgG2, IgG3, IgG4, or IgM isotype.
10. The anti-CCR8 antibody of embodiment 9, comprising a kappa light constant region.
11. The anti-CCR8 antibody of embodiment 4, wherein the C-terminal lysine of the heavy chain is truncated.
12. The anti-CCR8 antibody of embodiment 1, wherein the antibody is a humanized antibody.
13. A method of treating solid tumors, the method comprising administering the composition of embodiment 6 to a patient in need thereof.
14. A polynucleotide comprising a nucleotide sequence encoding an anti-CCR8 antibody, wherein the antibody comprises (i) a VH chain comprising three CDRs; and (ii) a VL chain comprising three CDRs, wherein:
   VH CDR#1 is GFIFSNAVMY (SEQ ID NO:1);
   VH CDR#2 is RIKTKFNNYATYYADAVKG (SEQ ID NO:2);
   VH CDR#3 is GDRNKPFAY (SEQ ID NO:3);
   VL CDR#1 is RASTSVITLLH (SEQ ID NO:4);
   VL CDR#2 is GASNLES (SEQ ID NO:5); and
   VL CDR#3 is QQSWNDPYT (SEQ ID NO:6).
15. An expression vector comprising the polynucleotide of embodiment 14.
16. A eukaryotic host cell transfected with the vector of embodiment 15.
17. The eukaryotic host cell of embodiment 16, which is a mammalian host cell.
18. A method of producing an anti-CCR8 antibody, comprising: (a) culturing the eukaryotic host cell of claim 15 and (b) recovering the anti-CCR8 antibody.
19. A method of treating solid tumors, the method comprising administering the composition according to embodiment 6 to a patient in need thereof.
20. An anti-CCR8 antibody having one or more of the following properties:
   (a) cross reactivity with cynomolgus CCR8;
   (b) poor ability to block CCL1/CCR8 interaction;
   (c) enhanced ability to induce ADCC;
   (d) enhanced binding to Fcγ receptors; and
   (e) good immunosafety determined by cytokine release assay.
21. An anti-CCR8 antibody having the following properties:
   (a) cross reactivity with cynomolgus CCR8;
   (b) poor ability to block CCL1/CCR8 interaction;
   (c) enhanced ability to induce ADCC;
   (d) enhanced binding to Fcγ receptors; and
   (e) good immunosafety determined by cytokine release assay.
22. An anti-CCR8 antibody having the following properties:
   (a) cross reactivity with cynomolgus CCR8;
   (b) poor ability to block CCL1/CCR8 interaction;
   (c) enhanced ability to induce ADCC.
23. The anti-CCR8 antibody of any one of embodiments 19-21 which comprises (i) a VH chain comprising three CDRs; and (ii) a VL chain comprising three CDRs, wherein:
   VH CDR#1 is GFIFSNAVMY (SEQ ID NO:1);
   VH CDR#2 is RIKTKFNNYATYYADAVKG (SEQ ID NO:2);
   VH CDR#3 is GDRNKPFAY (SEQ ID NO:3);
   VL CDR#1 is RASTSVITLLH (SEQ ID NO:4);
   VL CDR#2 is GASNLES (SEQ ID NO:5); and
   VL CDR#3 is QQSWNDPYT (SEQ ID NO:6).
24. The anti-CCR8 antibody of any one of embodiments 20-22, wherein the antibody comprises a heavy chain variable region comprising the amino acid sequence set forth as SEQ ID NO: 7 and a light chain variable region comprising the amino acid sequence set forth as SEQ ID NO: 8.
25. The anti-CCR8 antibody of any one of embodiments 20-22, wherein the antibody comprises a heavy chain comprising the amino acid sequence set forth as SEQ ID NO: 9 and a light chain comprising the amino acid sequence set forth as SEQ ID NO: 10.

26. The anti-CCR8 antibody of any one of embodiments 20-22, wherein the antibody is afucosylated.
27. The anti-CCR8 antibody of any one of embodiments 20-22 which comprises (i) a VH chain comprising three CDRs; and (ii) a VL chain comprising three CDRs, wherein:
   VH CDR#1 is GFIFSNAVMY (SEQ ID NO:1);
   VH CDR#2 is RIKTKFNNYATYYADAVKG (SEQ ID NO:2);
   VH CDR#3 is GDRNKPFAY (SEQ ID NO:3);
   VL CDR#1 is RASTSVITLLH (SEQ ID NO:4);
   VL CDR#2 is GASNLES (SEQ ID NO:5); and
   VL CDR#3 is QQSWNDPYT (SEQ ID NO:6);
   and wherein the antibody is afucosylated.
28. A method of treating solid tumors, the method comprising administering a combination of the composition of embodiment 6 and a composition comprising anti-PD-1 antibody to a patient in need thereof.
29. The method of embodiment 28, wherein the anti-PD-1 antibody is selected from the group consisting of budigalimab, pembrolizumab, nivolumab, cemiplimab, and dostarlimab.
30. The method of embodiment 29, wherein the anti-PD-1 antibody is budigalimab.
31. The method of embodiment 29, wherein the anti-PD-1 antibody is pembrolizumab.
32. A method of treating solid tumors, the method comprising administering a combination of the composition of embodiment 6 and a composition comprising anti-PD-L1 antibody to a patient in need thereof.
33. The method of embodiment 32, wherein the anti-PD-L1 antibody is selected from the group consisting of atezolizumab, avelumab, durvalumab.
34. The method of embodiment 33, wherein the anti-PD-L1 antibody is atezolizumab.
35. The composition of embodiment 6, wherein about 70% or more, about 80% or more, about 90% or more, or about 100% or more of the anti-CCR8 antibodies in the composition are afucosylated.
36. The anti-CCR8 antibody according to any one of embodiments 2-4, wherein the antibody is afucosylated.
37. A composition comprising a plurality of the anti-CCR8 antibodies of embodiment 36.
38. The composition of embodiment 37, wherein about 70% or more, about 80% or more, about 90% or more, or about 100% or more of the anti-CCR8 antibodies in the composition are afucosylated.
39. An anti-CCR8 antibody comprising two heavy chains, each comprising the amino acid sequence set forth as SEQ ID NO: 9 and two light chains, each comprising the amino acid sequence set forth as SEQ ID NO: 10, wherein the antibody is afucosylated.
40. A composition comprising a plurality of the anti-CCR8 antibodies of embodiment 39.
41. The composition of embodiment 40, wherein about 70% or more, about 80% or more, about 90% or more, or about 100% or more of the anti-CCR8 antibodies in the composition are afucosylated.

What is claimed:

1. An anti-CCR8 antibody which comprises (i) a VH chain comprising three CDRs; and (ii) a VL chain comprising three CDRs, wherein:
   VH CDR#1 is GFIFSNAVMY (SEQ ID NO:1);
   VH CDR#2 is RIKTKFNNYATYYADAVKG (SEQ ID NO:2);
   VH CDR#3 is GDRNKPFAY (SEQ ID NO:3);
   VL CDR#1 is RASTSVITLLH (SEQ ID NO:4);
   VL CDR#2 is GASNLES (SEQ ID NO:5); and
   VL CDR#3 is QQSWNDPYT (SEQ ID NO:6).

2. The anti-CCR8 antibody of claim 1, wherein the antibody comprises a heavy chain variable region comprising the amino acid sequence set forth as SEQ ID NO: 7 and a light chain variable region comprising the amino acid sequence set forth as SEQ ID NO: 8.

3. The anti-CCR8 antibody of claim 1, wherein the antibody comprises a heavy chain comprising the amino acid sequence set forth as SEQ ID NO: 9 and a light chain comprising the amino acid sequence set forth as SEQ ID NO: 10.

4. The anti-CCR8 antibody according to claim 3, wherein the antibody is afucosylated.

5. A composition comprising a plurality of the anti-CCR8 antibodies of claim 1.

6. The composition of claim 5, wherein greater than 80% of the anti-CCR8 antibodies in the composition are afucosylated.

* * * * *

SEQUENCE LISTING

```
Sequence total quantity: 14
SEQ ID NO: 1            moltype = AA  length = 10
FEATURE                 Location/Qualifiers
source                  1..10
                        mol_type = protein
                        organism = synthetic construct
SEQUENCE: 1
GFIFSNAVMY                                                              10

SEQ ID NO: 2            moltype = AA  length = 19
FEATURE                 Location/Qualifiers
source                  1..19
                        mol_type = protein
                        organism = synthetic construct
SEQUENCE: 2
RIKTKFNNYA TYYADAVKG                                                    19

SEQ ID NO: 3            moltype = AA  length = 9
FEATURE                 Location/Qualifiers
source                  1..9
                        mol_type = protein
                        organism = synthetic construct
SEQUENCE: 3
GDRNKPFAY                                                                9

SEQ ID NO: 4            moltype = AA  length = 11
FEATURE                 Location/Qualifiers
source                  1..11
                        mol_type = protein
                        organism = synthetic construct
SEQUENCE: 4
RASTSVITLL H                                                            11

SEQ ID NO: 5            moltype = AA  length = 7
FEATURE                 Location/Qualifiers
source                  1..7
                        mol_type = protein
                        organism = synthetic construct
SEQUENCE: 5
GASNLES                                                                  7
```

```
SEQ ID NO: 6           moltype = AA  length = 9
FEATURE                Location/Qualifiers
source                 1..9
                       mol_type = protein
                       organism = synthetic construct
SEQUENCE: 6
QQSWNDPYT                                                                 9

SEQ ID NO: 7           moltype = AA  length = 120
FEATURE                Location/Qualifiers
source                 1..120
                       mol_type = protein
                       organism = synthetic construct
SEQUENCE: 7
EVQLVESGGG LVQPGGSLKL SCAASGFIFS NAVMYWVRQA SGKGLEWVAR IKTKFNNYAT         60
YYADAVKGRF TISRDDSKNM VYLQMNSLKT EDTAVYYCTA GDRNKPFAYW GQGTLVTVSS        120

SEQ ID NO: 8           moltype = AA  length = 107
FEATURE                Location/Qualifiers
source                 1..107
                       mol_type = protein
                       organism = synthetic construct
SEQUENCE: 8
ETVVTQSPAT LSLSPGERAT LSCRASTSVI TLLHWFQQKP GQAPRLLIHG ASNLESRVPA         60
RFSGSGSGTD FTLTISSLEP EDFATYFCQQ SWNDPYTFGQ GTKLEIK                     107

SEQ ID NO: 9           moltype = AA  length = 450
FEATURE                Location/Qualifiers
source                 1..450
                       mol_type = protein
                       organism = synthetic construct
SEQUENCE: 9
EVQLVESGGG LVQPGGSLKL SCAASGFIFS NAVMYWVRQA SGKGLEWVAR IKTKFNNYAT         60
YYADAVKGRF TISRDDSKNM VYLQMNSLKT EDTAVYYCTA GDRNKPFAYW GQGTLVTVSS        120
ASTKGPSVFP LAPSSKSTSG GTAALGCLVK DYFPEPVTVS WNSGALTSGV HTFPAVLQSS        180
GLYSLSSVVT VPSSSLGTQT YICNVNHKPS NTKVDKKVEP KSCDKTHTCP PCPAPELLGG        240
PSVFLFPPKP KDTLMISRTP EVTCVVVDVS HEDPEVKFNW YVDGVEVHNA KTKPREEQYN        300
STYRVVSVLT VLHQDWLNGK EYKCKVSNKA LPAPIEKTIS KAKGQPREPQ VYTLPPSREE        360
MTKNQVSLTC LVKGFYPSDI AVEWESNGQP ENNYKTTPPV LDSDGSFFLY SKLTVDKSRW        420
QQGNVFSCSV MHEALHNHYT QKSLSLSPGK                                        450

SEQ ID NO: 10          moltype = AA  length = 214
FEATURE                Location/Qualifiers
source                 1..214
                       mol_type = protein
                       organism = synthetic construct
SEQUENCE: 10
ETVVTQSPAT LSLSPGERAT LSCRASTSVI TLLHWFQQKP GQAPRLLIHG ASNLESRVPA         60
RFSGSGSGTD FTLTISSLEP EDFATYFCQQ SWNDPYTFGQ GTKLEIKRTV AAPSVFIFPP        120
SDEQLKSGTA SVVCLLNNFY PREAKVQWKV DNALQSGNSQ ESVTEQDSKD STYSLSSTLT        180
LSKADYEKHK VYACEVTHQG LSSPVTKSFN RGEC                                   214

SEQ ID NO: 11          moltype = AA  length = 449
FEATURE                Location/Qualifiers
source                 1..449
                       mol_type = protein
                       organism = synthetic construct
SEQUENCE: 11
EVQLVESGGG LVQPGGSLKL SCAASGFIFS NAVMYWVRQA SGKGLEWVAR IKTKFNNYAT         60
YYADAVKGRF TISRDDSKNM VYLQMNSLKT EDTAVYYCTA GDRNKPFAYW GQGTLVTVSS        120
ASTKGPSVFP LAPSSKSTSG GTAALGCLVK DYFPEPVTVS WNSGALTSGV HTFPAVLQSS        180
GLYSLSSVVT VPSSSLGTQT YICNVNHKPS NTKVDKKVEP KSCDKTHTCP PCPAPELLGG        240
PSVFLFPPKP KDTLMISRTP EVTCVVVDVS HEDPEVKFNW YVDGVEVHNA KTKPREEQYN        300
STYRVVSVLT VLHQDWLNGK EYKCKVSNKA LPAPIEKTIS KAKGQPREPQ VYTLPPSREE        360
MTKNQVSLTC LVKGFYPSDI AVEWESNGQP ENNYKTTPPV LDSDGSFFLY SKLTVDKSRW        420
QQGNVFSCSV MHEALHNHYT QKSLSLSPG                                         449

SEQ ID NO: 12          moltype = DNA  length = 1410
FEATURE                Location/Qualifiers
source                 1..1410
                       mol_type = other DNA
                       organism = synthetic construct
SEQUENCE: 12
atggaattcg gcctgagctg gctgttcctg gtggccatcc tgaagggcgt gcagtgcgaa         60
gtccagctgg ttgaatctgg cggaggactg gttcagcctg gcggatctct gaagctgtct        120
tgtgccgcca gcggcttcat cttcagcaac gccgtgatgt actgggtccg acaggcctct        180
ggcaaaggcc tggaatgggt cgccagaatc aagaccaagt tcaacaacta cgccacctac        240
tacgccgacg ccgtgaaggg cagattcacc atcagcaggg acgacagcaa gaacatggtg        300
```

```
tacctgcaga tgaacagcct gaaaaccgag gacaccgccg tgtactactg cacagccggc    360
gacagaaaca agcccttttgc ctattggggc cagggcaccc tggttaccgt tagctctgcc    420
tccaccaagg gcccatcggt cttcccctg gcacctcct ccaagagcac ctctgggggc     480
acagcggccc tgggctgcct ggtcaaggac tacttcccg aaccggtgac ggtgtcgtgg    540
aactcaggcg ccctgaccag cggcgtgcac accttcccgg ctgtcctaca gtcctcagga    600
ctctactccc tcagcagcgt ggtgaccgtg ccctccagca gcttgggcac ccagacctac    660
atctgcaacg tgaatcacaa gcccagcaac accaaggtgg acaagaaagt tgagcccaaa    720
tcttgtgaca aaactcacac atgcccaccg tgcccagcac ctgaactcct ggggggaccg    780
tcagtcttcc tcttcccccc aaaacccaag gacaccctca tgatctcccg gacccctgag    840
gtcacatgcg tggtggtgga cgtgagccac gaagacctg aggtcaagtt caactggtac    900
gtggacggcg tggaggtgca taatgccaag acaaagccgc gggaggagca gtacaacagc    960
acgtaccgtg tggtcagcgt cctcaccgtc ctgcaccagg actggctgaa tggcaaggag    1020
tacaagtgca aggtctccaa caaagcctc ccagcccca tcgagaaaac catctccaaa     1080
gccaaagggc agccccgaga accacaggtg tacaccctgc cccatcccg ggaggagatg    1140
accaagaacc aggtcagcct gacctgcctg gtcaaaggct tctatcccag cgacatcgcc   1200
gtggagtggg agagcaatgg gcagccggag aacaactaca agaccacgcc tcccgtgctg   1260
gactccgacg gctccttctt cctctacagc aagctcaccg tggacaagag caggtggcag   1320
caggggaacg tcttctcatg ctccgtgatg catgaggctc tgcacaacca ctacacgcag   1380
aagagcctct ccctgtctcc gggcaaatga                                     1410

SEQ ID NO: 13          moltype = DNA  length = 711
FEATURE                Location/Qualifiers
source                 1..711
                       mol_type = other DNA
                       organism = synthetic construct
SEQUENCE: 13
atggacatgc gggtgcccgc ccagctgctg ggacttctgc tgctgtggtt ccccggcagc     60
agatgcgaga cagtggtcac acagtctccc gccacactgt cactgtctcc aggcgaaaga   120
gccacactga gctgtagagc cagcaccagc gtgatcacac tgctgcactg gttccagcag   180
aagcctggac aggctcccag actgctgatt cacggcgcca gcaacctgga aagcagagtg   240
cctgccagat tttccggcag cggctctggc accgatttca ccctgaccat aagcagcctg   300
gaacctgagg acttcgccac ctactttttgc cagcagagct ggaacgaccc ctacaccttt   360
ggccagggcc caagctgga aatcaagcga actgtggctg caccatcgt cttcatcttc    420
ccgccatctg atgagcagtt gaaatctgga actgcctctg ttgtgtgcct gctgaataac   480
ttctatccca gagaggccaa agtacagtgg aaggtggata acgccctcca atcgggtaac   540
tcccaggaga gtgtcacaga gcaggacagc aaggacagca cctacagcct cagcagcacc   600
ctgacgctga gcaaagcaga ctacgagaaa cacaaagtct acgcctgcga agtcacccat   660
cagggcctga gctcgcccgt cacaaagagc ttcaacaggg gagagtgtta g              711

SEQ ID NO: 14          moltype = AA  length = 12
FEATURE                Location/Qualifiers
source                 1..12
                       mol_type = protein
                       organism = synthetic construct
SEQUENCE: 14
CTAGDRNKPF AY                                                         12
```